(12) United States Patent
Sproul

(10) Patent No.: US 9,505,706 B2
(45) Date of Patent: Nov. 29, 2016

(54) PREPARATION OF LIPOAMINO ACIDS AND LIPOPEPTIDES USING SALTS AS CO-REACTANTS

(71) Applicant: University of South Carolina, Columbia, SC (US)

(72) Inventor: Gordon Sproul, Beaufort, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/830,082

(22) Filed: Aug. 19, 2015

(65) Prior Publication Data

US 2016/0052869 A1  Feb. 25, 2016

Related U.S. Application Data

(60) Provisional application No. 62/040,068, filed on Aug. 21, 2014.

(51) Int. Cl.
*A61K 38/00* (2006.01)
*C07K 1/00* (2006.01)
*C07C 231/02* (2006.01)
*C07K 1/107* (2006.01)
*C07B 43/06* (2006.01)

(52) U.S. Cl.
CPC ............ *C07C 231/02* (2013.01); *C07K 1/1077* (2013.01); *C07B 43/06* (2013.01); *C07K 1/00* (2013.01)

(58) Field of Classification Search
None
See application file for complete search history.

(56) References Cited

PUBLICATIONS

Varasteanu et al. U.P.B. Sci. Bull., Series B, vol. 73, Iss. 3, 2011, pp. 147-154.*

* cited by examiner

*Primary Examiner* — Patrick Lewis
(74) *Attorney, Agent, or Firm* — Dority & Manning, P.A.

(57) ABSTRACT

Methods for synthesizing a lipoamino acid and a lipopeptide are provided. The method can include reacting a fatty acid with an amino acid or a peptide and a co-reactant salt to form a lipoamino acid or a lipopeptide, respectively. The co-reactant salt is generally a magnesium sulfate, magnesium carbonate, potassium carbonate, iron (II) sulfide (troilite), or a mixture thereof.

20 Claims, 8 Drawing Sheets

PREPARATION OF LIPOAMINO ACIDS AND LIPOPEPTIDES USING SALTS AS CO-REACTANTS

PRIORITY INFORMATION

The present application claims priority to U.S. Provisional Patent Application Ser. No. 62/040,068 titled "Preparation of Lipoamino Acids and Lipopeptides Using Salts as Co-Reactants" of Gordon Sproul filed on Aug. 21, 2014, the disclosure of which is incorporated by reference herein.

BACKGROUND

Lipid membranes, present in all three domains of life, serve the crucial function of separating chemicals of cellular life from an aqueous environment. Thus, the lipid world has been proposed as one possibility for how life began (Monnard and Deamer 2002), postulating that protolife began in a lipid-protected environment. Membranes of current cells are composed of amphipathic phospholipids. A major challenge for theories suggesting such a lipid bilayer for protolife is that phosphate was essentially unavailable for prebiotic chemistry due to its insolubility in the presence of divalent cations that were likely present (Pasek 2008). Despite the advantage that a lipid membrane provides for establishing a protected chemical environment for protolife, it seems unlikely that phospholipids formed the earliest membranes.

Alternatively, a peptide world is postulated in which peptides have been recognized as central to the origin of life. Since peptides currently provide numerous biological functions, their necessity early in the development of life has been obvious. The coupling of amino acids to form peptides has been extensively investigated. Formation of peptides by dehydration condensation of amino acids has included wetting/drying cycles (Schwendinger 1995), high temperatures (Fox and Middlebrook 1954; Shock 1993; Sakata, Kitadai and Yokoyama 2010), high pressures (Otake 2011), adsorption (Gururani, Pant, Pandey and Pandey 2012; Lambert 2008), hygroscopic salts (Kitadai, Yokoyama and Nakashima 2011), activating agents (Hulshof and Ponnamperuma 1976; Brack 1982), dehydrating agents (Lambert 2008) and near saturation of water with sodium chloride combined with copper(II) salts (Lahav and Chang 1982; Rode and Schwendinger 1990; Rode, Fitz and Jakschitz 2007). Although there is no general agreement on which conditions were relevant in producing early peptides, several conceivable candidate conditions have been described in which peptides' amide bonds could have formed from the ammonium and carboxylate groups of amino acids.

Currently, cellular membranes are composed of about half lipids and half proteins (Rondel et al. 2009) and their co-evolution is likely (Mulkidjanian, Galperin and Koonin 2009; Mulkidjanian and Galperin 2010). Cells of many bacterial (Asselineau 1991) and eukaryotic species contain a ubiquitous amphipathic group of lipoamino acids, lipopeptides and lipoproteins. Their presence in Archaea is dubious (Dibrova, Galperin and Mulkidjanian, 2014; but see Bodour, Drees and Maier 2003; Kebbouche-Gana et al. 2009). These compounds typically consist of a fatty acid bound to the amino acid or peptide by an amide bond. The widespread occurrence in at least two of the three domains is possibly indicative of life's conservation of these biomolecules that have proven to be of significant advantage throughout evolutionary time.

Dehydration condensation reactions of amino acids are likely similar to reactions between fatty acids and amino acids that could also form amide bonds. Similar reaction conditions could have generated peptides along with lipoamino acids and lipopeptides on the early Earth.

SUMMARY

Objects and advantages of the invention will be set forth in part in the following description, or may be obvious from the description, or may be learned through practice of the invention.

Methods are generally provided for synthesizing a lipoamino acid. In one embodiment, the method includes reacting a fatty acid with an amino acid and a co-reactant salt to form a lipoamino acid. The co-reactant salt is generally a magnesium sulfate, magnesium carbonate, potassium carbonate, iron (II) sulfide (troilite), or a mixture thereof.

Methods are also generally provided for synthesizing a lipopeptide. In one embodiment, the method includes reacting a fatty acid with a peptide in the presence of a salt to form a lipopeptide. The co-reactant salt is generally magnesium sulfate, magnesium carbonate, potassium carbonate, iron (II) sulfide (troilite), or a mixture thereof.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1A:
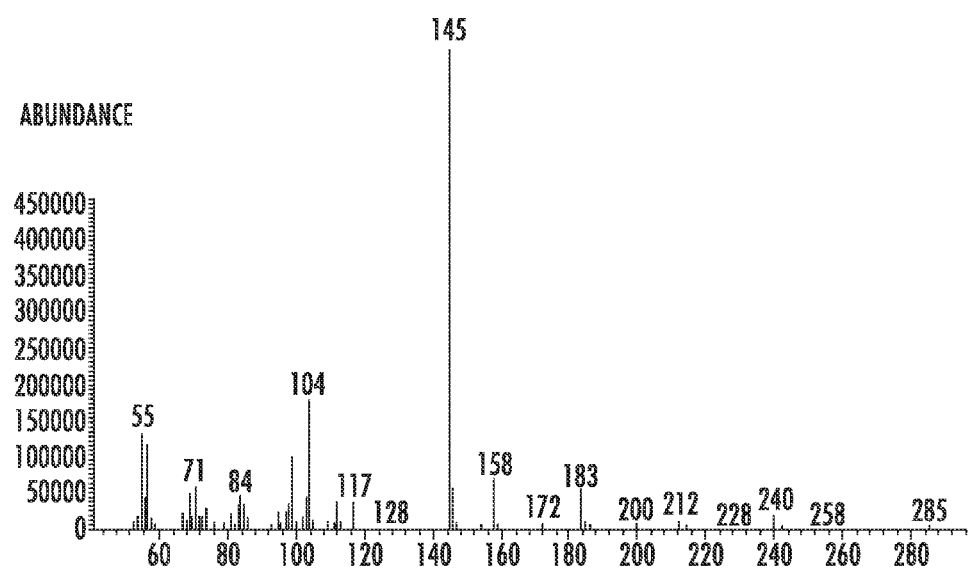
FIGS. 1A and 1B show, respectively, the gas chromatographs of both a sample of N-lauroyl glycine ethyl ester produced by standard organic synthetic procedures and one of the same compound produced by means of the described invention, using a salt at elevated temperatures and after ethyl esterification.
Figure 1B:
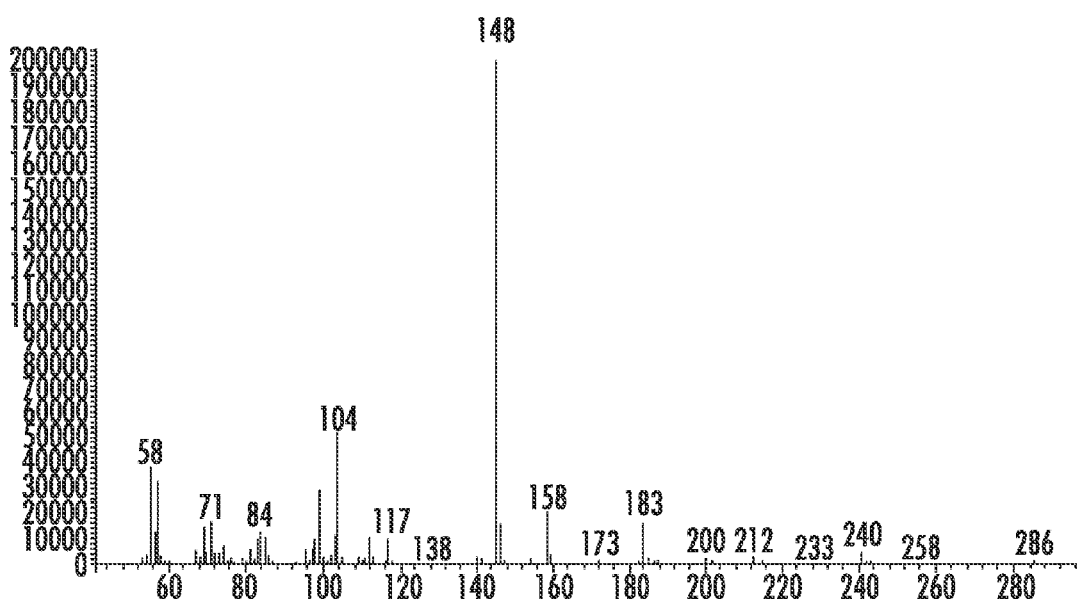

Repeat use of reference characters in the present specification and drawings is intended to represent the same or analogous features or elements of the present invention.

DEFINITIONS

Chemical elements are discussed in the present disclosure using their common chemical abbreviation, such as commonly found on a periodic table of elements. For example, hydrogen is represented by its common chemical abbreviation H; iron is represented by its common chemical abbreviation Fe; and so forth.

The term "organic" is used herein to refer to a class of chemical compounds that are comprised of carbon atoms along with atoms of other elements. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, a "saturated" carbon chain means that all the carbon to carbon bonds in the hydrocarbon chain are single bonds, allowing the maximum number of hydrogens to bond to each carbon, thus the chain is "saturated" with hydrogen atoms. Conversely, an "unsaturated" hydrocarbon chain means that the carbon chain contains at least one carbon-to-carbon double or triple bond, thereby reducing the number of hydrogens present on the chain. A monounsaturated hydrocarbon chain contains one carbon-to-carbon double bond, while a polyunsaturated hydrocarbon chain contains at least two carbon-to-carbon double bonds.

As is known in the organic chemistry arts, the term "alkyl" refers to monovalent saturated aliphatic hydrocarbyl groups having from 1 to 24 carbon atoms and preferably 1 to 10 carbon atoms. This term includes, by way of example, linear and branched hydrocarbyl groups such as methyl (—$CH_3$), ethyl (—$CH_2CH_3$), n-propyl (—$CH_2CH_2CH_3$), isopropyl (($CH_3)_2$CH—), n-butyl ($CH_3CH_2CH_2CH_2$—), isobutyl (($CH_3)_2CHCH_2$—), sec-butyl (($CH_3$)($CH_3CH_2$)CH—) and t-butyl (($CH_3)_3$C—). The term "heteroalkyl" refers to alkyl groups in which one or more C atoms are substituted by oxygen, nitrogen, sulfur, or combinations thereof.

"Cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain 3 to 15, 3 to 10, 3 to 8, 3 to 6, 4 to 6, 3 to 5, or 5 or 6 ring-forming carbon atoms. Ring-forming carbon atoms of a cycloalkyl group can be optionally substituted by nitrido, oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like.

A "substituted alkyl" refers to an alkyl described herein in which one or more hydrogen atoms attached to carbon of the alkyl is replaced by another group, such as halogen, aryl, substituted aryl, cycloalkyl, substituted cycloalkyl, and combinations thereof. Suitable substituted alkyls include, for example, benzyl and trifluoromethyl.

As is known in the organic chemistry arts, the term "aryl" refers to an aromatic carbocyclic group from 5 to 14 carbon atoms having a single ring (e.g., benzo) or multiple condensed rings (e.g., diphenyl, naphthyl or anthryl) in which some condensed rings may or may not be aromatic. The term "heteroaryl" refers to an aromatic group that contains at least one heteroatom (e.g., oxygen, nitrogen, sulfur, or combinations thereof) within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom.

"Substituted aryl" refers to aryl described herein in which one or more hydrogen atoms attached to any carbon atoms is replaced by one or more functional groups such as alkyl, substituted alkyl, cycloalkyl, substituted cycloalkyl, heterocycloalkyl, substituted heterocycloalkyl, halogen, halogenated alkyl (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Examples of substituted aryls include perfluorophenyl, chlorophenyl, 3,5-dimethylphenyl, 2,6-diisopropylphenyl and the like.

As is known in general and inorganic chemistry, the term "salt" refers to ionic compounds that contain positively charged cations and negatively charged anions. The cations may be composed of individual positively charged elements called monatomic cations or a collection of elements that are collectively positively charged called polyatomic cations. Examples of monatomic cations are sodium ions, calcium ions, iron (II) ions, copper (I) ions and magnesium ions. Examples of polyatomic cations are mercury (I), pyridinium, and ammonium. The anions may be composed of individual negatively charged elements called monatomic anions or a collection of elements that are negatively charged called polyatomic anions. Examples of monatomic anions are chloride anion, oxygen anion and sulfur anion; examples of polyatomic anions include carbonate, phosphate, nitrate, acetate and hydroxide. Minerals are naturally occurring ionic or quasi-ionic substances that can be loosely termed salts because of their ionic make-up.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally provided for synthesizing lipoamino acids and lipopeptides via a reaction of an amino acid with a fatty acid and a co-reactant salt. Specifically, the carboxyl group of the fatty acid reacts with the amino group of the amino acid (i.e., the N-terminus) to form an amide bond therebetween and releasing a molecule of water ($H_2O$). Thus, the reaction is a dehydration synthesis reaction (also known as a condensation reaction). The resulting —C(O)NH— bond is an amide bond, and the resulting molecule is an amide, generally described as a lipoamino acid or a lipopeptide. In one embodiment, a polypeptide can be used instead of a single amino acid as a reactant with a fatty acid to form a lipopeptide. Specifically, the N-terminus of the polypeptide reacts with the carboxylic acid group of the fatty acid in a similar dehydration synthesis reaction.

Each of the reactants, along with the reaction conditions, is discussed in greater detail below.

I. Amino Acids and Peptides

Amino acids are organic compounds that include an amine functional group (—NH$_2$ or NHR) and a carboxylic acid functional group (—COOH), along with a side-chain specific to each amino acid. Amino acids having both the amine and the carboxylic acid groups attached to the first (alpha-) carbon atom have particular importance in biochemistry, including the 20 proteinogenic amino acids, which combine into peptide chains ("polypeptides") to form the building-blocks of a vast array of proteins. These amino acids are known as 2-, alpha-, or α-amino acids, and have the generic formula:

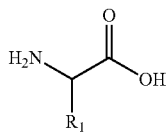

Formula 1: Generic Amino Acid where R$_1$ is an organic substituent, such as an alkyl group, a heteroalkyl group, a cycloalkyl group, a substituted alkyl group, an aryl group, a heteroaryl group, or a substituted aryl group. Particularly suitable amino acids include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or mixtures thereof. Other less common alpha-amino acids include sarcosine and ornithine. Beta- and gamma amino acids are similar but include one or two additional carbon atoms between the carboxylic acid and amine groups, respectively. Each of these amino acids can exist in either the D- or L-forms, which specify the "handedness" of the molecule.

As both the amine and carboxylic acid groups of amino acids can react to form amide bonds, one amino acid molecule can react with another and become joined through an amide linkage. This condensation reaction yields the newly formed peptide bond and a molecule of water. Reaction of multiple amino acids together (i.e., polymerization of multiple amino acids) forms a polypeptide with an N-terminus (i.e., an amine group) and a C-terminus (a carboxylic acid group).

II. Fatty Acids

Fatty acids are organic compounds that include a carboxylic acid group attached to a long aliphatic tail. Generically, a fatty acid has the chemical formula:

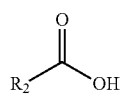

Formula 2: Generic Fatty Acid where R$_2$ represents a hydrocarbon chain, either saturated or unsaturated (including both monounsaturated and polyunsaturated fatty acids) and either straight chain, branched chain or multichain. According to the present disclosure, the hydrocarbon chain of the fatty acid can be of any length, such as comprising from about 8 to about 22 carbons Many fatty acids have common names, relating to their corresponding hydrocarbon chain, to describe the acid. The hydrocarbon chains can also be described by the number of carbon atoms present in the chain and the number and location of any double bonds present in the chain, represented by n:m$^{\Delta p, p', p''}$, where n is the number of carbons in the hydrocarbon chain, m is the number of carbon-to-carbon double bonds in the chain, p is the location of the first double bond (if present), p' is the location of the second double bond (if present), p'' is the location of the third double bond (if present), and so on, The $^{\Delta x}$ nomenclature denotes each double bond, where the double bond is located on the xth carbon-to-carbon bond, numbered from the carboxylic acid carbon.

Particularly suitable examples of saturated fatty acids that can be used to react with an amino acid to form a lipoamino acid and/or a lipopeptide according to the presently disclosed methods include, but are not limited to, caprylic acid (8:0), lauric acid (12:0), tridecylic acid (13:0), myristic acid (14:0), pentadecylic acid (15:0), cetylic acid (16:0, also known as palmitic acid), heptadecanoic acid (17:0), and stearic acid (18:0). Particularly suitable examples of unsaturated fatty acids that can be used to react with an amino acid to form a lipoamino acid and/or a lipopeptide according to the presently disclosed methods include, but are not limited to, palmitoleic acid (16:1$^{\Delta 9}$), oleic acid (18:1$^{\Delta 9}$), linoleic acid (18,2$^{\Delta 9,12}$), conjugated linoleic acid (18:2$^{\Delta 9,11}$), linolenic acid (18:3$^{\Delta 9,12,15}$), and γ-linolenic acid (18:3$^{\Delta 6,9,12}$)

III. Co-Reactant Salts

Without wishing to be bound by any particular theory, it is believed that the co-reactant salt reacts with the amino acid and/or fatty acid during the reaction process, and also aids the reaction's removal of water coupled with elevated temperatures. Generally, the reaction requires an approximately equimolar amount of salt to fatty acid to form the lipoamino acids and lipopeptides. For example, the molar ratio of salt to fatty acid can be about 0.5:1 to about 2.5:1 (that is, the salt is present in a molar amount that is about 50% to about 250% of the molar amount of the fatty acid), such as about 1:1 to about 2:1.

Particularly suitable salts and minerals for use in the provided methods include, but are not limited to, magnesium sulfate, magnesium carbonate, potassium carbonate, iron (II) sulfide, (troilite), or mixtures thereof.

IV. Reaction Method

As discussed above, the formation of lipoamino acids and lipopeptides is generally provided through a dehydration reaction of the N-terminus of an amino acid or a polypeptide with a fatty acid in the presence of a salt. In most embodiments, the reaction can be performed at a reaction temperature of about 30° C. to about 200° C., such as about 80° C. to about 160° C. (e.g., 115° C. to about 160° C.).

The relative amounts of the (I) amino acid/peptide or combination of amino acids/peptides, (II) fatty acid or combination of fatty acids, and (III) dehydration salt or combination of salts can be adjusted based upon the particular reactants chosen. In certain embodiments, the molar ratio of the amino acid/peptide to the fatty acid is about 0.5:1 to about 5:1 (that is, the amino acid/peptide is present in a molar amount that is about 50% to about 500% of the molar amount of the fatty acid), such as about 1:1 to about 4:1.

Upon reaction, a lipoamino acid or a lipopeptide is covalently bonded through the reaction of the carboxyl group of the fatty acid with the amino group of the amino acid (or the N-terminus of a polypeptide) to form an amide bond therebetween and releasing a molecule of water (H$_2$O). For example, Formula 3 shows a generic lipoamino acid formed from the dehydrogenation reaction of an amino acid of Formula 1 and a fatty acid of Formula 2:

Formula 3: Generic Lipoamino Acid

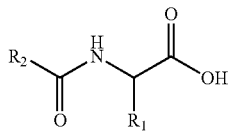

where $R_1$ is an organic substituent (as discussed above with respect to Formula 1) and $R_2$ is represents a hydrocarbon chain (as discussed above with respect to Formula 2).

In one particular embodiment, the lipoamino acids and lipopeptides formed from the methods provided herein can be further reacted with an alcohol in an esterification reaction to form an ester. For example, the alcohol ($R_3OH$) can be reacted with the lipoamino acid of Formula 3 to form the ester of Formula 4:

Formula 4: Generic Lipoamino Ester

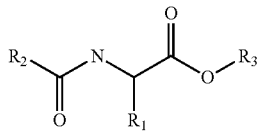

where $R_1$ is an organic substituent (as discussed above with respect to Formula 1); $R_2$ represents a hydrocarbon chain (as discussed above with respect to Formula 2), and $R_3$ is an organic substituent (such as those discussed above with respect to Formula 1).

EXAMPLES

Heating in a manner similar to that used to produce peptides from amino acids was chosen as the simplest means for testing the possibility of forming dehydration condensation products between fatty acids and amino acids, thereby coupling the two proposed worlds: the Peptide World and the Lipid World. The first successful experiment that produced a lipoamino acid, N-laruoylglycine (LG) gave only 0.4% of the desired product. Evaluation of several variables provided more advantageous conditions for the formation of these types of compounds. While experiments with numerous agents were by-and-large negative, magnesium sulfate and magnesium carbonate produced high yields of LG. This corresponds with other recent findings that magnesium salts are superior to those of strontium, barium or lithium for the polymerization of glycine and far superior to salt-free dehydrations. Temperature and time experiments indicated that higher temperatures even above 150° C. and longer times up to several weeks produced higher ratios of the desired acyl amino acids. Again, these results are in line with those found for the dimerization of glycine. The strong amide bonding of two essential prebiotic species—peptides and fatty acids—could help explain how protolife first became encapsulated. Having both lipids and peptides covalently bound, protolife would have had the advantages of the biophysical and biochemical differences of both of these substances: a membrane boundary as well as peptides that could be used for biochemical processes. Various authors have recognized the necessity of both biomolecules for the formation of the protocell.

The likelihood of this proposed Lipopeptide World can be demonstrated in numerous ways. Salts and acids of lipopeptides have been shown to combine with cationic surfactants to form vesicles as well as liposomes, and lipopeptides alone form lamellar structures. Therefore, it is possible that such compounds could have formed membranes of prebiotic cells. Phosphate was likely to be in very limited supply to protolife due to its insolubility in oceans with high calcium concentrations. Although current life forms all have membranes composed of phospholipids, it is unlikely that protocells could have had the means to acquire phosphates. Since lipopeptides are surfactants with a polar head and nonpolar tail, they could have provided early protective membranes. Intriguingly, an N-acyl onithine lipid has been found in the bacterium *Deleya marin*, a species that replaces its phospholipid membrane when *D. marina* is grown under phosphate-limited conditions. N-acyl ornithine has a structure that is comparable to the N-acyl phosphatidylethanolamine it replaces, having both a hydrophobic tail and zwitterionic head. Use of a lipoamino acid in contemporary life forms demonstrates the feasibility of the potential use of lipoamino acids by protolife and may be a vestigial remnant of its primordial existence.

Experimental:

The chemicals used in these experiments were purchased from several suppliers. L-alanine, glycine, iron (II) sulfide, magnesium carbonate, potassium carbonate, stearic acid, sulfuric acid, and black-capped two-dram vials equipped with polytetrafluoroethylene (PTFE) lined caps came from Fisher; lauric acid and methyl t-butyl ether (MTBE) were from Alpha Aesar; glycylglycine came from Sigma; thionyl chloride came from Fluka; hexanes were from Mallinckrodt; and oxalyl chloride came from Acros.

To prepare a known N-lauroyl glycine (LG) sample, the acyl chloride of the fatty acid was prepared using oxalyl chloride (Adams and Ulich 1920) and lauric acid (LA). The N-lauroyl glycine (LG) was then prepared with glycine using standard methods (Varasteanu et al. 2011) along with a few drops of pyridine (Montalbetti and Falque 2005) gave 87% yield for this "standard". For analysis by gas chromatography and mass spectrometry (GC/MS), LG was esterified to determine both retention time and mass spectrum of the ethyl ester of N-lauroyl glycine (LGE). In a similar fashion, N-lauroyl glycylglycine (LGG) was prepared using thionyl chloride (Bauer, 1946) and esterified with ethanol to give the ethyl ester (LGGE). Here and elsewhere, the percentage yield is the percentage of the indicated product compared with the sum of all products containing the fatty acid. The fatty acid ester thereby served as an internal standard to determine percentage yield.

Heating lauric acid with glycine for a week at 140° C. produced small amounts (<1%) of LG, so various dehydrating agents were added in an effort to enhance the yield. In a characteristic dehydration reaction, 0.500 mmol of the fatty acid, 0.500-2.000 mmol of the amino acid or dipeptide, and 0.500-2.000 mmol of various salts were added, ground, deaerated, sealed with PTFE tape and a black PTFE-lined cap, and heated from 115° C. to 160° C. for a given amount of time ranging from hours to weeks. On removal the contents were esterified, separated into aqueous and nonaqueous layers and the organic layer collected for analysis. A wide range of salts, temperatures and reaction times were employed in order to increase yield. In similar ways N-lauroyl alanine and N-stearoyl alanine were prepared using magnesium carbonate and/or potassium carbonate. A 1:3 sample of lauric acid to glycine was also reacted with 0.20 g iron(II) sulfide at various temperatures.

The esterified samples were analyzed by gas chromatography with a mass selective detection (Hewlett-Packard 5890GC/5972MSD). The gas chromatograph was equipped with a 30 m×0.25 mm Zebron-5HT capillary column (Phenomenex Inc, Torrance, Calif.). The oven temperature was held at 120° C. for 0.5 minutes and then programmed to 200° C. at a rate of 8° C./min, then 250° C. at 4° C./min and held at the final temperature for up to 35 minutes. A split mode of injection (50:1) was used. Other general conditions of analysis included helium carrier gas at 30 cm/sec and the detector and injection port temperatures at 280° C. and 320° C. respectively. The mass chromatogram and mass spectrum were used for quantitative and qualitative analysis of the reaction products. Acylamino acid esters' mass spectra of the simpler amino acids and dipeptide were characterized by a molecular ion and/or McLafferty rearrangement ions, and high molecular weight peaks were correlated with structures. Both the GC scans and the MS spectra were output along with the integrated peak areas from the scan. Yields of the lipoamino acid or lipopeptide were determined by integrating MS peak areas of these and comparing against total areas of all fatty-acid-containing peaks. Parent ion peaks were observable with some of the products and the McLafferty peaks were critical for confirming the ester product. Retention times and MS spectra of the compounds were compared with those of compounds prepared using standard synthetic methods and with data bases. Infrared spectra using a Perkin-Elmer Spectrum One in transmission mode were collected using 4 cm-1 resolution with quadruple scans between 4000 and 450 $cm^{-1}$.

Figure 2:
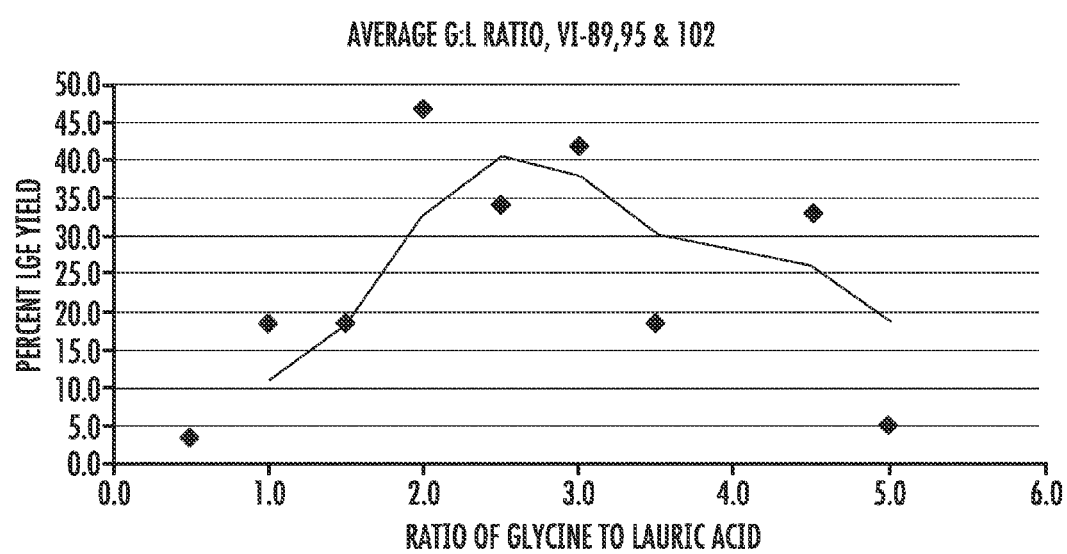
FIG. 2 shows a chart of the percentage yields of N-lauroylglycine ethyl ester as a function of the average glycine to lauric acid ratio, averaged from three series of ratios.
Figure 3:
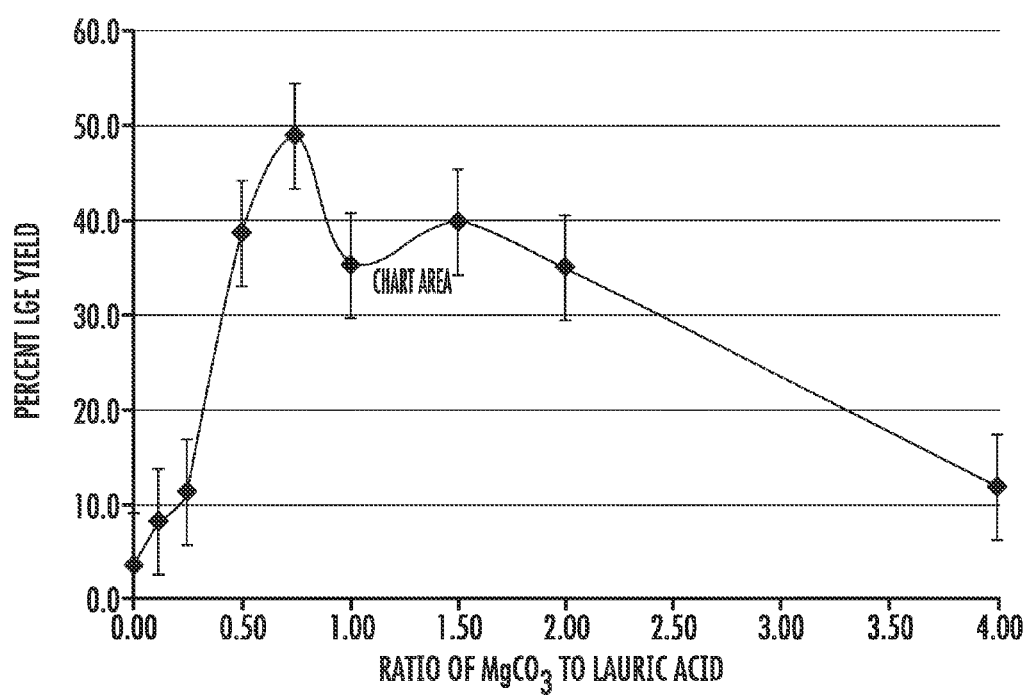
FIG. 3 shows a chart of the percentage yield of N-lauroylglycine ethyl ester as a function of the average ratio of magnesium carbonate to lauric acid, averaged over six series of ratios.

Results:

In order to determine the feasibility of synthesizing a lipoamino acid, one of the simplest members of this extensive group was selected for initial attention; the twelve-carbon containing lauric acid (dodecanoic acid) with glycine. Using common procedures, a standard sample of LGE was prepared for comparison against the compound made with a salt. Identification of LGE was straightforward using GC/MS: the strongest MS peak above 50 amu occurred at 145 amu, the McLafferty rearrangement cation of the ethyl glycine moiety (FIGS. 1A & B, the standard and the result from heating with magnesium carbonate, respectively). Initial efforts to produce the condensation product had yielded very small amounts (<1%) of product. Since this condensation reaction requires removal of water, it seemed reasonable that a dehydrating agent, coupled with elevated temperatures, could aid in this reaction. Several different dehydrating agents were tried, and while most gave only marginal increases in yield, $MgSO_4$ on esterification produced up to 6% of the desired LGE under unoptimized conditions. GC/MS analysis infrequently showed a slight amount of unesterified lauric acid with a retention time of 8.6 minutes, ethyl laurate (LE) at 9.1 minutes and LGE at 18.1 minutes. The parent ion peak, although small, was present at 285 amu (molecular mass of LGE is 285.4 amu) and the McLaferty peak appeared at 145 amu; see FIGS. 1A & B). Infrared scans showed absorption lines at 3319, 3079, 1647 and 1552 $cm^{-1}$ (Fox and Harada 1960; Viedma 2000). Various parameters were analyzed to increase yields. Undeaerated samples undergoing prolonged heating at 150° C. darkened considerably to deep amber, likely indicating air decomposition. Deaerating samples with $N_2$ prior to heating decreased the darkening. Increasing the temperature to 150° C. essentially doubled the reaction rate compared to 140° C. Visually comparing results of an unground with that of a thoroughly ground mixture showed the product of the unground sample to have a splotchy coloration with a significantly diminished yield; therefore, it was necessary to scrupulously grind all mixtures prior to heating. Increasing the ratio of amino acid to lauric acid increased the yield significantly (FIG. 2). Keeping the ratio of salt about equal to that of lauric acid provided the best results (FIG. 3). It was necessary to average several data sets due to large random errors in yield results. Despite carefully controlled preparation techniques, yields of LGE from both repeated preparations of reacting compounds and even from subdivided samples of the same mixture produced wide ranges of product yields.

Figure 1C:
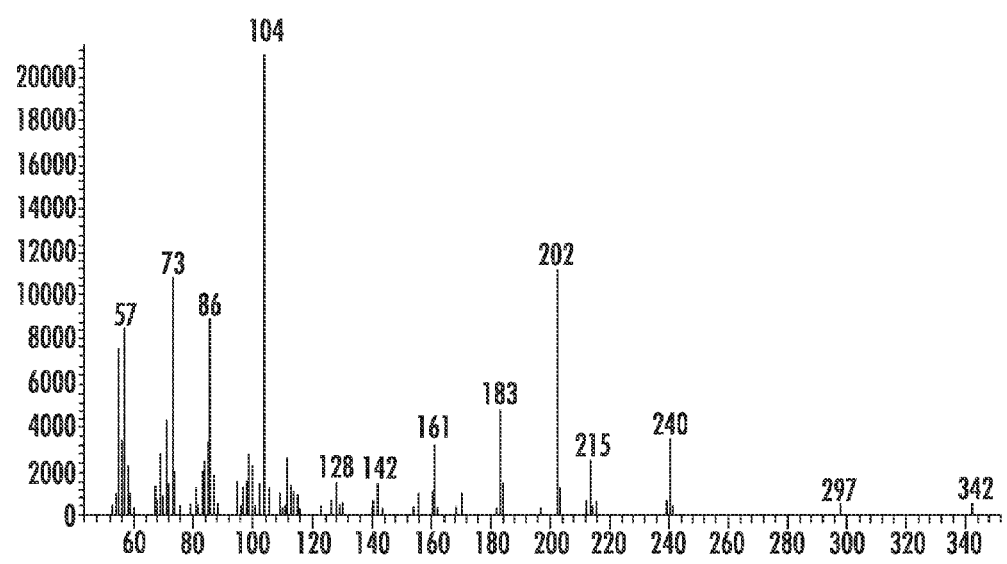
FIGS. 1C and 1D show, respectively, the gas chromatographs of both a sample of N-lauroyl glycylglycine ethyl ester produced by standard organic synthetic procedures and one of the same compound produced by means of the described invention, using a salt at elevated temperatures and after ethyl esterification.
Figure 1D:
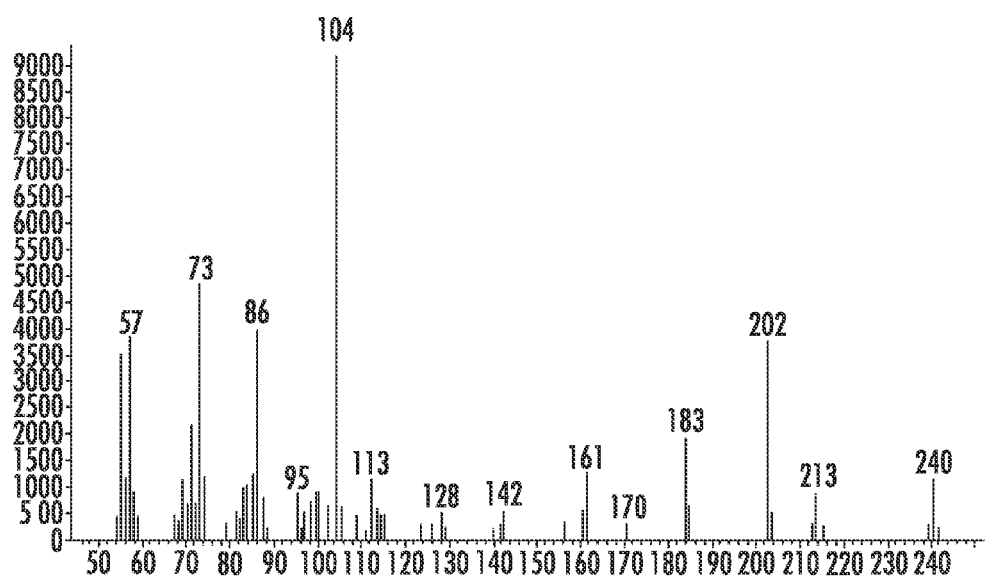
Figure 1E:
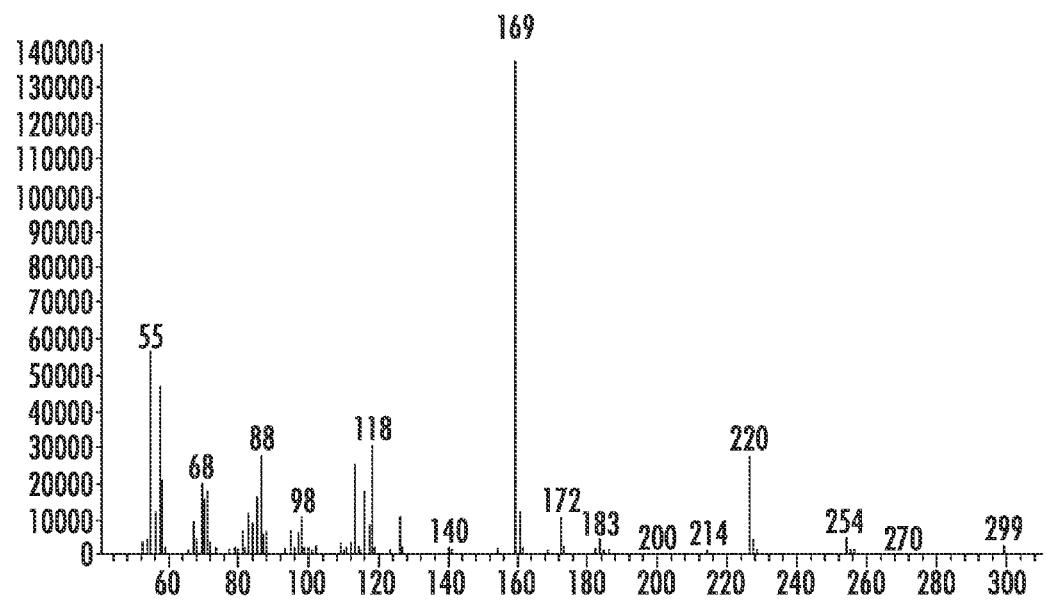
FIGS. 1E and 1F show, respectively, the gas chromatographs of both a sample of N-lauroyl alanine ethyl ester and one of the N-steroyl alanine ethyl ester produced by means of the described invention, using a salt at elevated temperatures and after ethyl esterification.
Figure 1F:
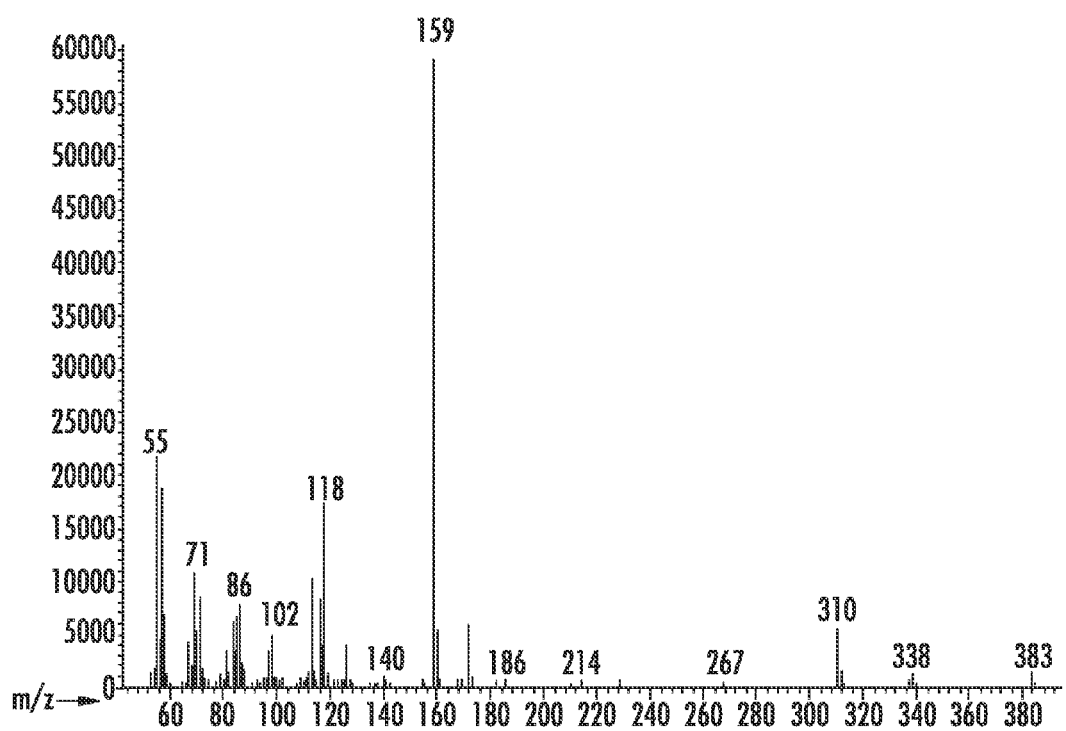

In order to evaluate the possibility of producing a lipopeptide by a similar method, glycylglycine was reacted with lauric acid and various salts. Both magnesium carbonate and potassium carbonate produced about one percent of the desired N-lauroylglycylglycine (FIGS. 1C & D, the standard LGGE and esterified product from heating with potassium carbonate, respectively) with a retention time of 30.2 minutes. The parent ion peak, although small, was present at 342 amu (molecular mass of LGE is 342.4 amu) and the McLaferty peak appeared at 202 amu. Ethyl esters of N-lauroyl alanine and N-stearoyl alanine (FIGS. 1E & F, respectively) were prepared in a manner similar to that of LGE, with retention times of 17.5 and 30.5 minutes, respectively, with McLaferty peaks at 159 as expected for the alanine group. Additionally, numerous other amino acids were condensed with lauric acid, but because of the presence of active functional groups, their MS spectra were more complex due to rearrangements, and conventional syntheses have not yet been carried out to confirm them.

As indicated in the Introduction, numerous methods have been shown to produce peptides from amino acids. In order to extend experiments that demonstrate the possibility of simultaneous formation of lipoamino acids and lipopeptides during the formation of peptides, an alternative synthesis was carried out. Cody, Hagen and Sverjensky (2011) showed that peptides can be formed simply by heating an amino acid with pulverized metal sulfides. Several sulfides were used in a similar manner to couple lauric acid with glycine. Heating the organics with iron (II) sulfide at 120° C. for fourteen days produced a 54% yield of the LG, while heating at 100° C. gave a 2% yield after twenty-five days.

Discussion:

GC/MS of the esterified condensation product of glycine and lauric acid showed a retention time and spectrum essentially identical with a standard N-lauroylglycine ethyl ester. Similarly, the infrared spectrum showed absorption bands that confirmed formation of the amide bond in this product. Likewise, GC/MS of N-lauroylglycylglycine ethyl ester synthesized using a salt showed both the same retention time and spectrum as N-lauroylglycylglycine ester prepared by standard methods. While yields of condensation products were significantly increased by optimizing several parameters, yields from comparable batches were inconsistent and varied widely. It seems likely that this random error occured because of the heterogeneous nature of the reaction mixture. Although the lauric acid melts at around 40° C., which would provide a liquid medium for reaction, both glycine and the various salts or minerals would remain as solids. As can be seen from FIG. 3, the salt-enhanced reaction appears to require an approximately equimolar amount of salt to fatty acid to form the acylamino acid. Grinding and sampling likely produce a range of particle sizes, some with smaller surface areas available for interaction with the reactants. Without access to a salt surface, the fatty acid or amino groups may be unable to readily form an amide bond.

Several possible condensation methods for forming peptides from amino acids have been published as indicated in the Introduction. Since current life forms rely extensively on proteins for nearly all biochemical functions many researchers have accepted the presence of peptides in protocells as a necessary condition for the first steps toward the living cell in a peptide world. The side chains of various amino acids can provide sites for coordination to transition metals and for bonding to various reactive species such as coenzymes, providing the wide-ranging chemical flexibility life has utilized. Alternatively, the very definition of life implies the necessity of a membrane separating the cell from an aqueous environment; such separation could well have been a prerequisite for protolife. For that reason many have promoted the lipid membrane as essential for protolife in a lipid world.

Formation of lipoamino acids by heating, in a manner similar to that in which peptides have been formed from amino acids has been demonstrated here and amplified by addition of various ionic compounds. While trials with numerous dehydrating agents were by-and-large negative, magnesium sulfate and magnesium carbonate produced high yields of LG. These results correspond with other recent findings that magnesium salts are superior to those of strontium, barium or lithium for the polymerization of glycine and far superior to salt-free dehydrations (Kitadai, Yokoyama and Nakashima 2011). Also, magnesium and calcium carbonates have been shown to increase the formation of alanine oligomers under hydrothermal conditions (Kawamura et al. 2011). The presence of both Lewis acid and Brønsted/Lowry base sites in these substances seem to serve vital roles in enhancing these reactions (Rimola, Sodupe and Ugliengo 2007). Temperature and time experiments indicated that higher temperatures even above 150° C. and longer times up to several weeks produced higher ratios of the desired acyl amino acids. Again, these results are in line with those found for the dimerization of glycine (Shock 1993; Sakata, Kitadai and Yokoyama 2010). Numerous authors have recognized the necessity of both peptides and amphipathic compounds (Monnard and Deamer 2002; Bywater 2009; Egel 2009) for the formation of the protocell. The strong amide bonding found in both peptides and lipoamino acid/lipopeptides that can be formed under similar conditions could help explain how protolife first became encapsulated, functioning and evolving. Having both lipids and peptides covalently bound, protolife would have had the advantages of the biophysical and biochemical characteristics of both of these substances: a lipid membrane boundary as well as peptides that could function in various biochemical processes.

The likelihood of this proposed lipopeptide world as a realistic realm in which the chemistry of protolife could have evolved has been demonstrated in numerous ways. Salts and acids of lipopeptides have been shown to combine with cationic surfactants to form vesicles (Ambuehl 1993) as well as liposomes (Epand 1998), while lipopeptides alone form lamellar structures (Douy and Gallot 1986; Gallot and Diao 1992). It is possible that mixtures of such compounds could have formed membranes of prebiotic cells. Mulkidjanian and Galperin (2010) recognize that single-tailed lipids were more likely present in proto-membranes than the more complex molecules that are currently found. Additionally, these same authors indicate that it is unlikely that glycerol was present in protobionts of bacteria; while one and two carbon species are formed readily by geochemical processes, three carbon containing species are not common.

Although all three domains of life have membranes composed of phospholipids, it is unlikely that early protocells could have had the means to acquire phosphates. Since lipopeptides are phosphate-free amphipathic compounds, they could have provided protective membranes for protocells without the need for phosphate. Intriguingly, when the bacterium *Deleya marin* is grown under phosphate-limited conditions, it replaces its phospholipid membrane with the phosphate-free lipoamino acid N-acyl onithine. N-acyl ornithine has a structure that is comparable to the N-acyl phosphatidylethanolamine that it replaces (Yagi, Corzo and Nakahara 1997). Use of this lipoamino acid in a contemporary life form demonstrates both the feasibility of lipopeptides as capable alternatives in forming the lipid bilayer and the possible retention of lipopeptides as relics of a primordial necessity. Lipopeptides, surfactants that required neither the difficult-to-obtain phosphates nor the three-carbon glycerol molecule, could have provided a membrane for protolife. It remains to be seen if other methods that have been used to produce peptides can be shown to also produce lipopeptides. Such efforts are underway in my laboratory.

Conclusion:

Lipoamino acids are surfactants that behave in a manner similar to phospholipids found in cellular membranes, and may represent vestigial biomolecules of prebiotic organisms. Since they do not include phosphate, they could have provided protolife with a suitable membrane that avoided the need for unobtainable phosphate. Using elevated temperatures, lipoamino acids and a lipopeptide have been synthesized by heating the reactants along with ionic compounds, in a manner that parallels reactions used to synthesize peptides. Certain salts, including magnesium sulfate, magnesium carbonate, potassium carbonate and iron (II) sulfide, enhance yields exponentially. This procedure is only one example of many potential prebiotic processes that form the amide bond; other condensation processes will likely also produce these compounds. With the potential encapsulation provided by lipopeptides along with the prospective metabolism inherent in a peptide surface, lipopeptides are proposed to have been critical for prebiotic development. A lipopeptide world is proposed in which these compounds allowed evolution of biophysically protected and biochemically active protolife.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of synthesizing a lipoamino acid, the method comprising:
   reacting a fatty acid with an amino acid and a co-reactant salt to form a lipoamino acid, wherein the co-reactant salt comprises magnesium sulfate, magnesium carbonate, potassium carbonate, iron (II) sulfide (troilite), or a mixture thereof.

2. The method as in claim 1, wherein the molar ratio of the amino acid to the fatty acid is about 0.5:1 to about 5:1.

3. The method as in claim 1, wherein the amino acid comprises alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, other alpha- or of beta- or gamma amino acids or mixtures thereof.

4. The method as in claim 1, wherein the fatty acid comprises a saturated fatty acid.

5. The method as in claim 4, wherein the saturated fatty acid comprises caprylic acid, lauric acid, tridecylic acid, myristic acid, pentadecylic acid, cetylic acid, heptadecanoic acid, stearic acid, arachidic acid, behenic acid or mixtures thereof or of branched chain saturated fatty acid comprises straight chain fatty acids with one or more alkyl groups bonded to carbons at various locations along the length of the chain.

6. The method as in claim 1, wherein the fatty acid comprises an unsaturated fatty acid.

7. The method as in claim 6, wherein the unsaturated fatty acid comprises palmitoleic acid, oleic acid, linoleic acid, conjugated linoleic acid, linolenic acid, γ-linolenic acid, or other unsaturated fatty acids with either or both cis and/or trans configurations at the double bond(s) or mixtures thereof.

8. The method as in claim 1, wherein the reaction is performed at a reaction temperature of about 30° C. to about 160° C.

9. The method as in claim 1, wherein the salt consists of an ionic or quasiionic compound or mixture of such compounds.

10. The method as in claim 1, wherein the cation of the salt consists of monatomic or polyatomic ions and the anion of the salt consists of monatomic or polyatomic ions or mixtures thereof.

11. The method as in claim 1, wherein the molar ratio of salt to fatty acid is about 0.5:1 to about 2.5:1.

12. The method as in claim 1, wherein the molar ratio of salt to fatty acid is about 1:1 to about 2:1.

13. The method as in claim 1, wherein the molar ratio of the amino acid or peptide to the fatty acid is about 0.5:1 to about 5:1.

14. A method of synthesizing a lipopeptide, the method comprising:

reacting a fatty acid with a peptide in the presence of a salt to form a lipopeptide, wherein the co-reactant salt comprises magnesium sulfate, magnesium carbonate, potassium carbonate, iron (II) sulfide (troilite), or a mixture thereof.

15. The method as in claim 14, wherein the molar ratio of the amino acid or peptide to the fatty acid is about 0.5:1 to about 5:1.

16. The method as in claim 14, wherein the fatty acid comprises a saturated fatty acid, and wherein the saturated fatty acid comprises caprylic acid, lauric acid, tridecylic acid, myristic acid, pentadecylic acid, cetylic acid, heptadecanoic acid, stearic acid, arachidic acid, behenic acid or mixtures thereof or of branched chain saturated fatty acid comprises straight chain fatty acids with one or more alkyl groups bonded to carbons at various locations along the length of the chain.

17. The method as in claim 16, wherein the fatty acid comprises an unsaturated fatty acid, and wherein the unsaturated fatty acid comprises palmitoleic acid, oleic acid, linoleic acid, conjugated linoleic acid, linolenic acid, γ-linolenic acid, or other unsaturated fatty acids with either or both cis and/or trans configurations at the double bond(s) or mixtures thereof. The method as in claim 1, wherein the reaction is performed at a reaction temperature of about 30° C. to about 160° C.

18. The method as in claim 14, wherein the salt consists of an ionic or quasiionic compound or mixture of such compounds.

19. The method as in claim 14, wherein the cation of the salt consists of monatomic or polyatomic ions and the anion of the salt consists of monatomic or polyatomic ions or mixtures thereof.

20. The method as in claim 14, wherein the molar ratio of salt to fatty acid is about 0.5:1 to about 2.5:1.

* * * * *